(12) United States Patent
Choe et al.

(10) Patent No.: US 9,226,685 B2
(45) Date of Patent: Jan. 5, 2016

(54) DENTAL RF COIL, HEAD-FIXING UNIT, AND MAGNETIC RESONANCE IMAGING SYSTEM INCLUDING SAME

(75) Inventors: Bo Young Choe, Seoul (KR); Dong Cheol Woo, Gyeongsangbuk-do (KR); Hyun Sub Ahn, Bucheon (KR)

(73) Assignee: Catholic University Industry Academic Cooperation Foundation, Seoul (KR)

( * ) Notice: Subject to any disclaimer, the term of this patent is extended or adjusted under 35 U.S.C. 154(b) by 694 days.

(21) Appl. No.: 13/522,686

(22) PCT Filed: Aug. 31, 2010

(86) PCT No.: PCT/KR2010/005867
§ 371 (c)(1),
(2), (4) Date: Jul. 17, 2012

(87) PCT Pub. No.: WO2011/090248
PCT Pub. Date: Jul. 28, 2011

(65) Prior Publication Data
US 2012/0288820 A1 Nov. 15, 2012

(30) Foreign Application Priority Data
Jan. 19, 2010 (KR) .................. 10-2010-0004874

(51) Int. Cl.
| | |
|---|---|
| *A61B 5/055* | (2006.01) |
| *A61B 5/00* | (2006.01) |
| *G01R 33/34* | (2006.01) |
| *G01R 33/341* | (2006.01) |
| *G01R 33/38* | (2006.01) |

(52) U.S. Cl.
CPC ............. *A61B 5/0555* (2013.01); *A61B 5/4542* (2013.01); *A61B 5/682* (2013.01); *G01R 33/34084* (2013.01); *A61B 5/4547* (2013.01); *G01R 33/341* (2013.01); *G01R 33/3806* (2013.01)

(58) Field of Classification Search
CPC .. A61B 5/0555; A61B 5/4542; A61B 5/4547; A61B 5/682; G01R 33/341; G01R 33/3806; G01R 33/34084
See application file for complete search history.

(56) References Cited

U.S. PATENT DOCUMENTS

| | | | | |
|---|---|---|---|---|
| 5,085,219 A | * | 2/1992 | Ortendahl et al. | 600/422 |
| 5,185,576 A | * | 2/1993 | Vavrek et al. | 324/318 |
| 5,692,027 A | * | 11/1997 | Yoshimura et al. | 378/38 |

(Continued)

FOREIGN PATENT DOCUMENTS

| | | |
|---|---|---|
| KR | 10-2002-0036063 A | 5/2002 |
| KR | 10-2008-0014769 A | 2/2008 |

*Primary Examiner* — Dixomara Vargas
(74) *Attorney, Agent, or Firm* — Joseph Hyosuk Kim; JHK Law

(57) ABSTRACT

The invention relates to an MRI system, comprising: an examination table including a cradle in which a patient may be positioned; a magnetic assembly disposed in the examination table and including first and second electrode assemblies, the respective electrode surfaces of which are disposed so as to be perpendicularly spaced apart by a certain distance and opposite each other such that space for imaging may be formed therebetween; and an RF coil unit contactingly or contactlessly attached to a part of a patient to be examined or an attached part corresponding to the part to be examined, applying an RF pulse to the part of the patient to be examined, and detecting an MR signal from the examined part.

3 Claims, 12 Drawing Sheets

(56) References Cited

U.S. PATENT DOCUMENTS

| | | | |
|---|---|---|---|
| 6,037,774 A * | 3/2000 | Felmlee et al. | 324/318 |
| 6,275,723 B1 * | 8/2001 | Ferris et al. | 600/417 |
| 6,441,612 B1 * | 8/2002 | Shimo et al. | 324/309 |
| 7,386,335 B2 * | 6/2008 | Eda et al. | 600/323 |
| 7,425,828 B2 * | 9/2008 | Garwood et al. | 324/310 |
| 7,612,562 B2 * | 11/2009 | Yasuhara | 324/318 |
| 7,619,415 B2 * | 11/2009 | Nakabayashi | 324/318 |
| 8,067,936 B2 * | 11/2011 | Garwood et al. | 324/307 |
| 8,744,162 B2 * | 6/2014 | Greenwood et al. | 382/132 |
| 8,847,597 B2 * | 9/2014 | Rasche et al. | 324/318 |
| 9,000,767 B2 * | 4/2015 | Schmidt | 324/318 |
| 2013/0190608 A1 * | 7/2013 | Schmidt | 600/422 |

* cited by examiner

US 9,226,685 B2

DENTAL RF COIL, HEAD-FIXING UNIT, AND MAGNETIC RESONANCE IMAGING SYSTEM INCLUDING SAME

CROSS-REFERENCE TO RELATED APPLICATION

This application is a National Phase application, filed under 35 U.S.C. §371, of PCT Application No. PCT/KR2010/005867, filed Aug. 31, 2010, which claims the benefit of priority to Korean Patent Application No. 10-2010-0004874, filed Jan. 19, 2010, the contents of which are incorporated herein by reference in their entirety.

TECHNICAL FIELD

The present invention relates to a magnetic resonance imaging system, and more particularly, to a dental RF (Radio Frequency) coil unit, a head-fixing unit, and an MRI (Magnetic Resonance Imaging) system including the same, which can be used for taking magnetic resonance images not only of teeth and the pubic bones but also of soft tissues, such as gums, and dental nerve tissues.

BACKGROUND ART

In general, CT (Computed Tomography) capturing systems, panoramic radiography equipment, cephalo imaging apparatuses, and so on are widely known as dental examination apparatuses used for diagnosing defects of teeth. Such imaging apparatuses are widely used as the basic examination apparatuses for diagnosing defects of teeth because they can rapidly make images of teeth conditions. However, because the imaging apparatuses all use X-rays, they can obtain excellent anatomical images about conditions of bones and horny tissues, such as teeth or pubic bones, but cannot obtain sufficient anatomical images about soft tissues, such as gums, and dental nerve tissues.

As an examination apparatus for obtaining higher image resolution and contrast about the soft tissues or the dental nerve tissues, an MRI (Magnetic Resonance Imaging) system using magnetic field is known. However, such an MRI system carries out examination while horizontally moving over a patient, who lies on a cradle, in a state where a magnetic field is shielded by a shielding device during the examination, and hence, the examination procedures are complicated and the patient may feel a fear of the examination in a closed space. Particularly, patients, who have claustrophobia, may refuse examination itself. Moreover, because conventional MRI system is designed to move over the whole body of the patient and requires the shielding device for shielding harmfulness by the magnetic field, the system is big in size and is very expensive. Furthermore, because the conventional MRI system uses a superconductive magnet and is designed to have a large imaging space so that the MRI system moves over the whole body of the patient, it is large in output quantity for operating the superconductive magnet, a gradient coil, an RF coil and so on, and hence, its maintenance fees and management fees are increased. Accordingly, the conventional MRI system is used only for emergencies or critical diseases, such as brain tumor and is rarely used for dental diagnosis, such as examinations of soft tissues, such as gums, and dental nerve tissues. For instance, MR images of soft tissues, such as gums, and dental nerve tissues for dental diagnosis are incidentally obtained and used when brain tumor or one of other critical diseases is examined.

Therefore, in order to conduct dental diagnosis to judge defects in the soft tissues, such as gums, and dental nerve tissues, development of a dental MRI system, which can easily and simply obtain MR images at lower costs, is demanded.

DISCLOSURE

Technical Problem

Accordingly, the present invention has been made in an effort to solve the above-mentioned problems occurring in the prior arts, and it is an object of the present invention to provide a dental RF (Radio Frequency) coil unit, a head-fixing unit, and an MRI (Magnetic Resonance Imaging) system including the same, which can easily, simply and precisely take MR images of teeth, the pubic bones, soft tissues, such as gums, or dental nerve tissues at lower costs, and which can be reduced in size.

Technical Solution

To achieve the above objects, the present invention provides an RF (Radio Frequency) coil unit including: an RF coil; and a support frame assembly in which the RF coil is supported, the support frame assembly being formed corresponding to an attached part including at least one of a patient's teeth and gums and the patient's face part where the teeth and gums are positioned.

Here, the RF coil may be a two-way RF coil in which an outgoing RF coil and an incoming RF coil are formed integrally.

The support frame assembly includes: one of a jaw rest having a jaw receiving recess formed corresponding to the face part, in which the patient's teeth and gums are positioned, and which includes the patient's jaw; a mask formed corresponding to the face part, in which the patient's teeth and gums are positioned; and a mouth piece formed corresponding to the patient's teeth and gums.

The jaw rest includes: a main body having a jaw receiving recess; and a support portion for supporting the patient's head not to be moved.

The support portion may be a pair of bars formed at both sides of the main body and getting in contact with the patient's ear part to support the patient's head part not to be moved in back and forth and right and left directions.

The mask includes: a main body formed corresponding to the face part, in which the patient's teeth and gums are positioned; and a fixing part formed on the main body for fixing the main body corresponding to the face part, in which the patient's teeth and gums are positioned.

Here, the main body may be formed in a round shape to surround the front face of the patient's face where the teeth and gums are positioned or in a "⌐" shape to surround the front face and sides of the patient's jaw.

The fixing part may be an ear holding part formed on the main body and held to the patient's ear part.

Selectively, the fixing part may be an elastic band connected to the main body such that the main body can be elastically fixed to the head part or the ear part.

In order to stably keep a state where the main body is in close contact with the patient's face part where the teeth and the gums are positioned when the fixing part fixes the main body to the patient's head part or ear part, the mask has a jaw support for supporting the jaw.

Selectively, the RF coil may include an outgoing RF coil and an incoming RF coil, which are formed separately. In this instance, the outgoing RF coil may be arranged in the jaw rest and the incoming RF coil may be arranged in the mask or the mouth piece.

In another aspect of the present invention, the present invention provides a head-fixing unit arranged on an examination table to fix a patient's head not to be moved and including a lateral movement limiting part for limiting a backward movement and a lateral movement of the head.

The lateral movement limiting part includes: a head rest arranged on a chair mounted on the examination table; first and second head bars arranged on the head rest for supporting right and left sides of the patient's head; and a guide rail formed on the head rest for supporting the first and second head bars to move to the head rest. Selectively, in order to move the first head bar in one direction and move the second head bar in the other direction, the lateral movement limiting part may have a pinion arranged between a first rack and a second rack respectively formed on the first and second head bars.

In order to limit a vertical movement of the head part, the head-fixing unit further includes a vertical movement limiting part. The vertical movement limiting part includes: a jaw rest having a jaw receiving recess for supporting the patient's jaw; and a jaw rest moving part arranged on the examination table for moving the jaw rest between a storing position and a jaw supporting position.

The jaw rest moving part includes: an arm having an end portion for fixing the jaw rest; a pivot shaft mounted on the examination table for movably supporting the other end portion of the arm; and a clamp for fixing the other end portion of the arm to the pivot shaft in a vertically movable manner.

Selectively, the jaw rest moving part may include: a support bar for supporting the jaw rest; a receiving bar mounted at the examination table for supporting the support bar to move vertically and rotate; and a clamp for fixing the support bar, which is accommodated in the receiving bar, not to be moved.

In a further aspect of the present invention, the present invention provides an MRI (Magnetic Resonance Imaging) system including: an examination table having a cradle in which a patient is positioned; a magnetic assembly arranged on the examination table and having first and second electrode assemblies in which pole faces are perpendicularly spaced apart from each other at a predetermined interval and opposed to each other such that an imaging space is formed; and an RF coil unit contactingly or contactlessly attached to one of the patient's examined part and the patient's attached part, the RF coil unit applying an RF pulse to the patient's examined part and detecting an RF signal from the examined part.

Here, the cradle may include a chair on which the patient can sit.

The first and second electrode assemblies may respectively include N-pole and S-pole permanent magnets.

The first and second electrode assemblies may be spaced apart from each other at an interval of about 30 cm or less.

The imaging space may be formed in an opened form at three parts out of the front part, the rear part, the upper part and the lower part. For this, the first and second electrode assemblies may be arranged at opposed end portions of a yoke having a lying-down C-shaped cross section.

The examined part includes the patient's teeth and gums, and the attached part includes at least one of the patient's teeth and gums and the patient's face part where the teeth and gums are positioned.

The RF coil unit includes: an RF coil; and an insulator assembly in which the RF coil is arranged, the insulator assembly formed corresponding to at least one of the examined part and the attached part.

In this instance, the RF coil may include a two-way RF coil in which an outgoing RF coil and an incoming RF coil are formed integrally. The insulator assembly includes: a jaw rest having a jaw receiving recess formed corresponding to the patient's attached part including the patient's jaw; a mask formed corresponding to the attached part, and a mouth piece formed corresponding to the examined part.

Selectively the RF coil may include an outgoing RF coil and an incoming RF coil separately formed. In this instance, the outgaining RF coil may be arranged in the jaw rest and the incoming RF coil may be arranged in the mask or the mouth piece.

In order to prevent detection of a bad MR signal due to the patient's movement, the MRI system according to the present invention further include a head-fixing unit arranged on the examination table for fixing the patient's head not to be moved during the examination.

The head-fixing unit may include a lateral movement limiting part for limiting a backward movement and a lateral movement of the head part. The lateral movement limiting part may include: a head rest arranged on the chair mounted on the examination table; first and second head bars arranged at the head rest for supporting right and left sides of the patient's head; and a guide rail formed on the head rest for supporting the first and second head bars to the head rest in a movable manner.

In order to limit a vertical movement of the head part, the head-fixing unit further includes a vertical movement limiting part. The vertical movement limiting part may include: a jaw rest having a jaw receiving recess for supporting the patient's jaw; and a jaw rest moving part arranged on the examination table for moving the jaw rest between a storing position and a jaw supporting position.

Moreover, the MRI system further includes: a lifting unit for lifting up and down the cradle during the examination. The lifting unit comprises: a driving motor; a pinion formed on a driving shaft of the driving motor; and a rack formed on the cradle to engage with the pinion.

Advantageous Effects

As described above, the MRI system including the dental RF coil unit and the head-fixing unit according to the present invention can reduce maintenance and management costs compared with the conventional MRI system using superconductive magnets because the first and second electrode assemblies according to the present invention are N-pole and S-pole permanent magnets.

Moreover, the MRI system including the dental RF coil unit and the head-fixing unit according to the present invention can reduce the entire size compared with the conventional MRI system because the first and second electrode assemblies are spaced apart from each other at an interval of 30 cm or less, and can also reduce maintenance and management costs because output quantity for driving the gradient coil and the RF coil is reduced.

Furthermore, the imaging space is constructed in such a way as to approach from three parts out of the front part, the rear part, the upper part and the lower part by the first and second electrode assemblies arranged at the opposed end portions of the yoke having the lying-down C-shaped cross section. Accordingly, the MRI system including the dental RF coil unit and the head-fixing unit according to the present invention can easily make an examination and reduce the patient's fear of examination because only the head part of the patient is positioned inside the imaging space without needing to position the patient's whole body inside the sealed examination table like the conventional MRI system.

Additionally, the RF coil unit is contactingly or contactlessly mounted corresponding to the patient's attached part, namely, the patient's teeth and gums or the patient's face part where the teeth and the gums are position during the examination. Accordingly, the MRI system including the dental RF coil unit and the head-fixing unit according to the present invention can obtain anatomical information of the soft tissues such as gums, tooth's nerve tissues, and so on more accurately than the conventional MRI system.

In addition, the head-fixing unit includes the lateral movement limiting part and the vertical movement limiting part for fixing the patient's head not to be moved. Therefore, the MRI system including the dental RF coil unit and the head-fixing unit according to the present invention can prevent detection of a bad MR signal due to the patient's movement, and hence, can obtain more correct and reliable MR images.

Furthermore, the MRI system including the dental RF coil unit and the head-fixing unit according to the present invention can make an examination while the patient who sits on the cradle is automatically lifted by the lifting unit, and hence, the patient can undergo the examination more comfortably in the MRI system according to the present invention than in the conventional MRI system.

MODE FOR INVENTION

Figure 1:
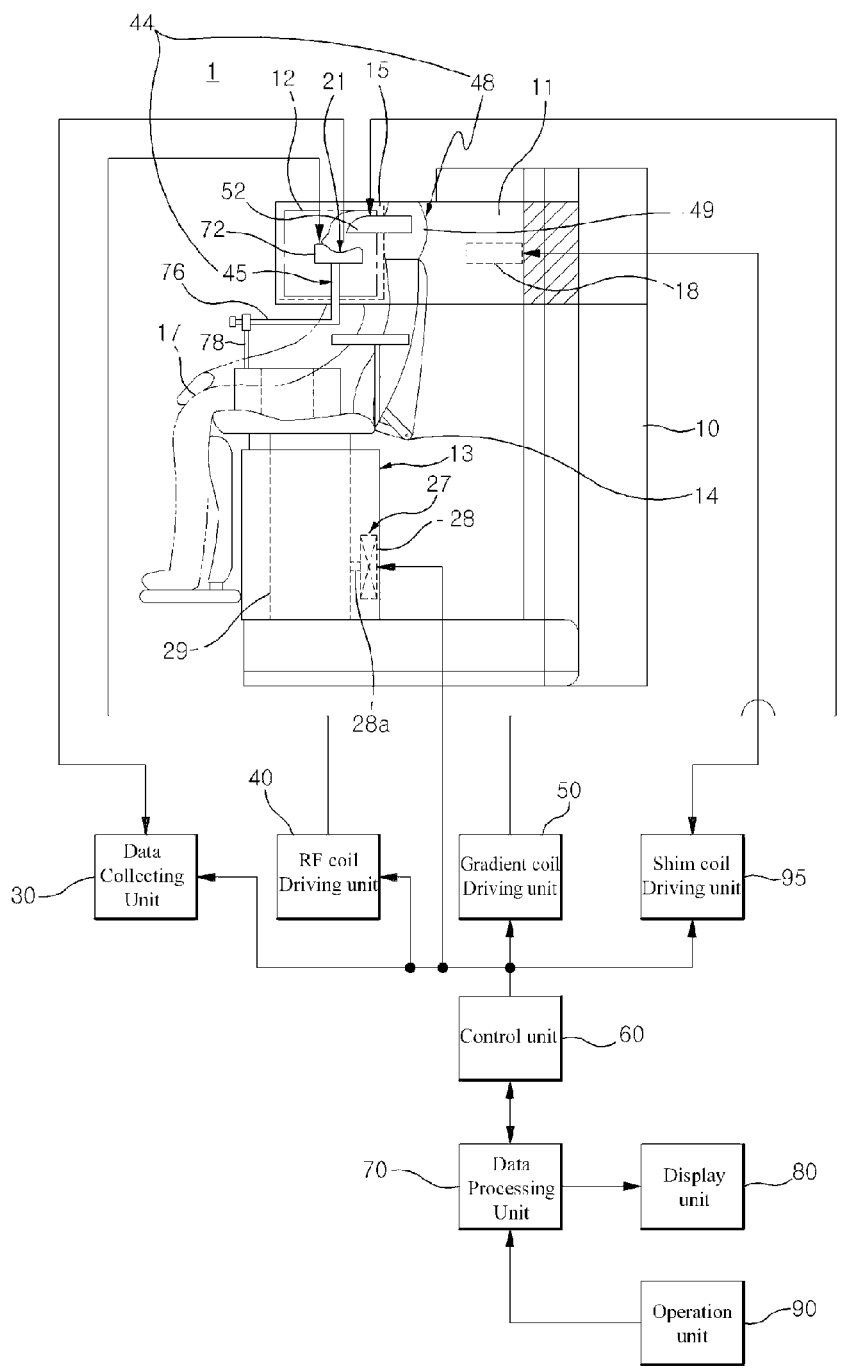
FIG. 1 is a schematic block diagram of an MRI (Magnetic Resonance Imaging) system according to a preferred embodiment of the present invention.

Reference will be now made in detail to MRI (Magnetic Resonance Imaging) system of the present invention with reference to the attached drawings.

First, referring to FIG. 1, the MRI (Magnetic Resonance Imaging) system according to a preferred embodiment of the present invention is described in detail as follows.

The MRI system 1 according to the present invention is to obtain MR images used for diagnosing defects of teeth, the pubic bones, soft tissues, such as gums, and dental nerve tissues, and includes an examination table 10, a magnetic assembly 12, a gradient coil unit 15, a shim coil unit 18, an RF (Radio Frequency) coil unit 21, a lifting unit 27, a data collecting unit 30, an RF coil driving unit 40, a gradient coil driving unit 50, a shim coil driving unit 95, a control unit 60, a data processing unit 70, a display unit 80, and a operation unit 90.

The examination table 10 is a structure where components of the MRI system 1 are mounted, and has a cradle 13, in which a patient 17 is positioned at an approximately central portion. The cradle 13 has a chair 14 on which the patient 17 can sit.

Moreover, in order to upwardly lift the patient's teeth and gum so that they can enter an imaging space 16 (see FIG. 2), which will be described later, or in order to downwardly lower them so that they can get out of the imaging space 16, the cradle 13 can be lifted up and down by the lifting unit 27. In this embodiment, the lifting unit 27 includes a driving motor 28. A pinion (not shown) having teeth is formed on a driving shaft 28a of the driving motor 28. A rack 29 having teeth engaging with the pinion is formed on an inner face of a lower portion of the chair 14. A gear train (not shown) for increasing a driving force of the driving motor 28 may be arranged between the pinion and the rack 29. Accordingly, when the driving motor 28 is rotated forwardly or reversely under the control of the control unit 60, the pinion formed on the driving shaft 28a is rotated to upwardly lift the rack 29 or to downwardly lower the rack 29, and hence, the chair 14, on which the patient sits, may be moved vertically by the rack 29.

In order to control the patient's seated position and posture, the entire of the cradle 14 may move back and forth using conventional back-and-forth moving means (not shown) or a backrest 14a of the chair 14 may be folded or unfolded at a predetermined angle using conventional angle-adjusting means (not shown).

As described above, because the MRI system 1 according to the present invention can carry out examination while the chair of the cradle 13, on which the patient 17 sits, is automatically elevated in a vertical direction by the lifting unit 27, compared with the conventional MRI system carrying out examination while the cradle, on which the patient 17 lies, moves in a horizontal direction, the MRI system 1 according to the present invention makes the patient 17 undergo the examination in comfort without fear.

Figure 2:
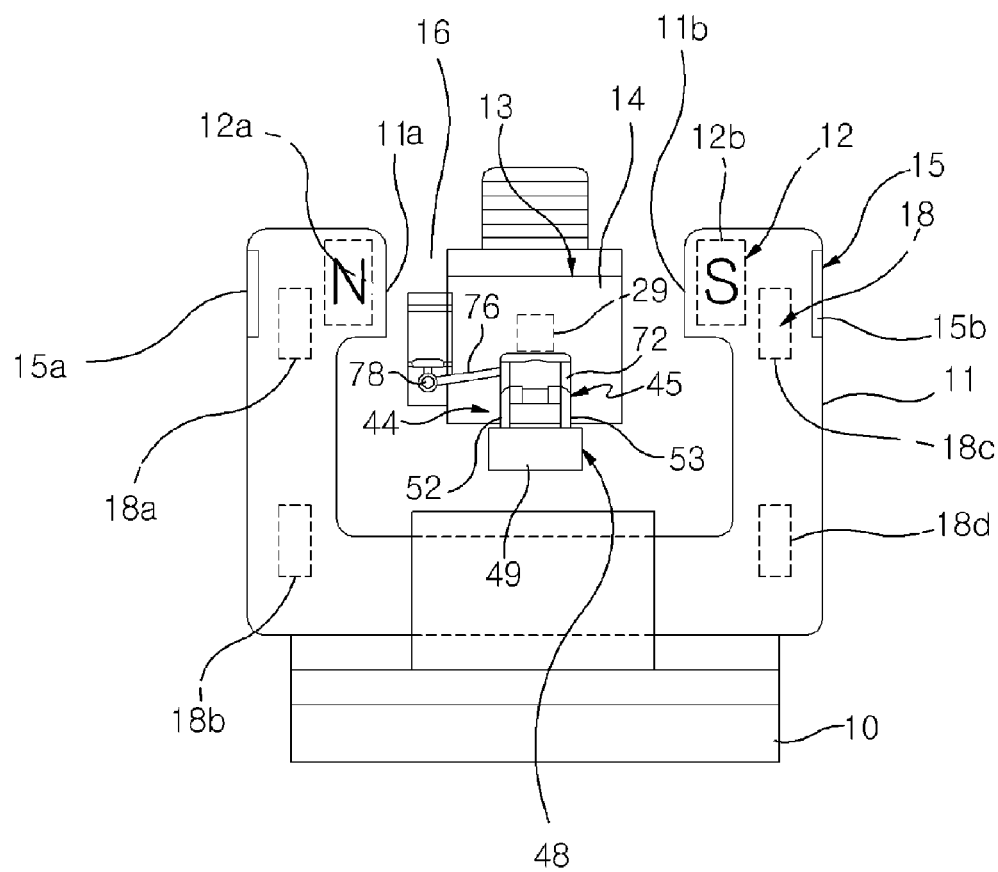
FIG. 2 is a plan view of the MRI system of FIG. 1.

As shown in FIG. 2, the magnetic assembly 12 forms a main magnetic field, and includes first and second electrode assemblies 12a and 12b formed on an yoke 11 arranged on an upper portion of the examination table 10. The first and second electrode assemblies 12a and 12b respectively have pole faces disposed so as to be perpendicularly spaced apart by a certain distance, preferably at an interval of about 30 cm or less, and opposed to each other such that the imaging space 16 is formed therebetween. In this embodiment, the first and second electrode assemblies 12a and 12b are respectively arranged at opposed end portions 11a and 11b of the yoke 11, which respectively have a lying-down C-shaped cross section. Furthermore, the first and second electrode assemblies 12a and 12b respectively have N-pole and S-pole permanent magnets. Accordingly, the magnetic field is formed in the shape of Alphabet C between the N pole and the S pole, and the imaging space 16 has an opened structure between the opposed end portions 11a and 11b of the yoke 11 so as to approach from a front portion, an upper portion and a lower portion of the examination table 10.

As described above, because the first and second electrode assemblies 12a and 12b respectively have the N-pole and S-pole permanent magnets spaced apart from each other at an interval of about 30 cm, which corresponds to the greatest size of a human being's head, the MRI system 1 is reduced in the entire size, and can reduce maintenance and management fees, which are generated when electric current is applied to the superconductive magnet in the conventional MRI system. Additionally, because the imaging space 16 is constructed in such a fashion that the patient's head approach the imaging space 16 from the tree directions, namely, from the front portion, the upper portion and the lower portion, there is no need that the patient 17 locates the whole body inside the imaging space 16 during the examination like the conventional MRI system. According to the present invention, because the patient locates only the head part inside the imaging space 16, the patient can easily undergo the examination with no fear of a sealed space.

As shown in FIG. 2, the gradient coil unit 15 forms a magnetic field having a magnetic variation slope of X, Y and Z directions in a direction of the main magnetic field so as to obtain three-dimensional images, and includes first and second gradient coils 15a and 15b respectively arranged on opposed faces of the opposed end portions 11a and 11b of the yoke 11 on which the first and second electrode assemblies 12a and 12b are located. The gradient coil driving unit 50 (see FIG. 1) operates the gradient coil unit 15 under the control of the control unit 60 to make the main magnetic field, which is formed by the magnetic assembly 12, have a magnetic variation slope.

The shim coil unit 18 make the main magnetic field formed by the magnetic assembly 12 uniform, and includes first to fourth shim coils 18a, 18b, 18c and 18d arranged in the magnetic field of the magnetic assembly 12.

The shim coil driving unit 95 (see FIG. 1) operates the shim coil unit 18 under the control of the control unit 60 to make the main magnetic field uniform.

As shown in FIGS. 1 to 4 and 16, the RF coil unit 21 applies an RF pulse to the teeth or the gum, which is a part of the patient to be examined, (hereinafter, called "the examined part") so as to form a high frequency magnetic field and receives an MR signal from the examined part during the examination. The RF coil unit 21 includes a support frame assembly 24 (see FIG. 16), which is formed to surround the front face, the sides and the rear face of the patient's jaw part including the patient's face (hereinafter, called "attached part") on which the examined part is located, and in which the RF coil 22 is arranged and supported.

Figure 16:
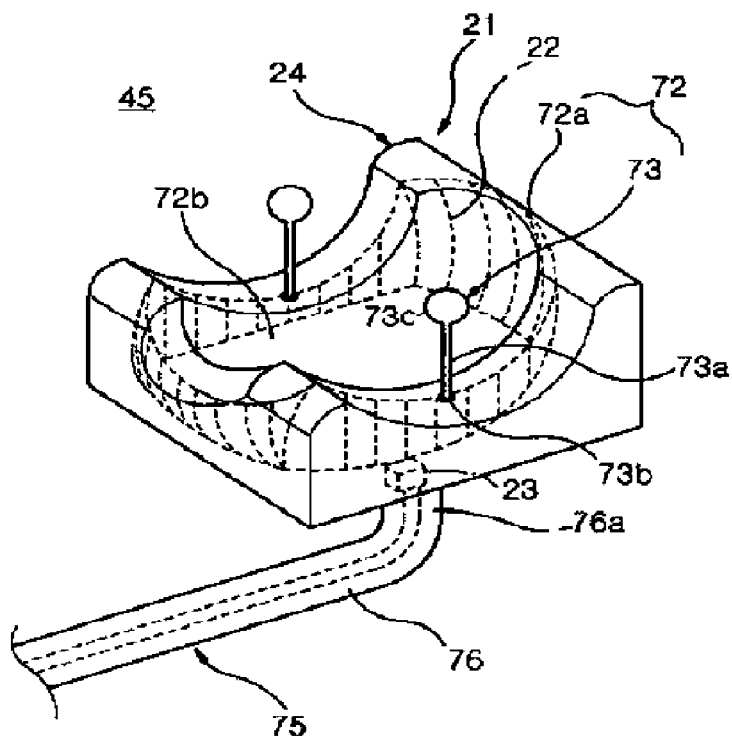
FIG. 16 is a perspective view of a jaw rest of a vertical movement limiting part of the head-fixing unit on which the RF coil unit of the MRI system of FIG. 1 is arranged.

Referring to FIG. 16, the support frame assembly 24 has a jaw rest 72. The jaw rest 72 includes a main body 72a formed in a hull shape, and a support portion 73 for supporting the patient's head not to be moved.

The main body 72a is made of an insulating material having appropriate mechanical strength to maintain an electromagnetic force generated when electric current is applied to the RF coil 22 and to keep the form of the RF coil 22 arranged therein. The main body 72a includes a jaw receiving recess 72b formed to correspond to the patient's jaw part for receiving the jaw part including the attached part, on which the examined part is located. The jaw receiving recess 72b is large enough to receive the patient's jaw part, which may be varied according to patients. The RF coil 22 is arranged inside front and rear side walls and right and left side walls of the main body 72a.

Figure 17:
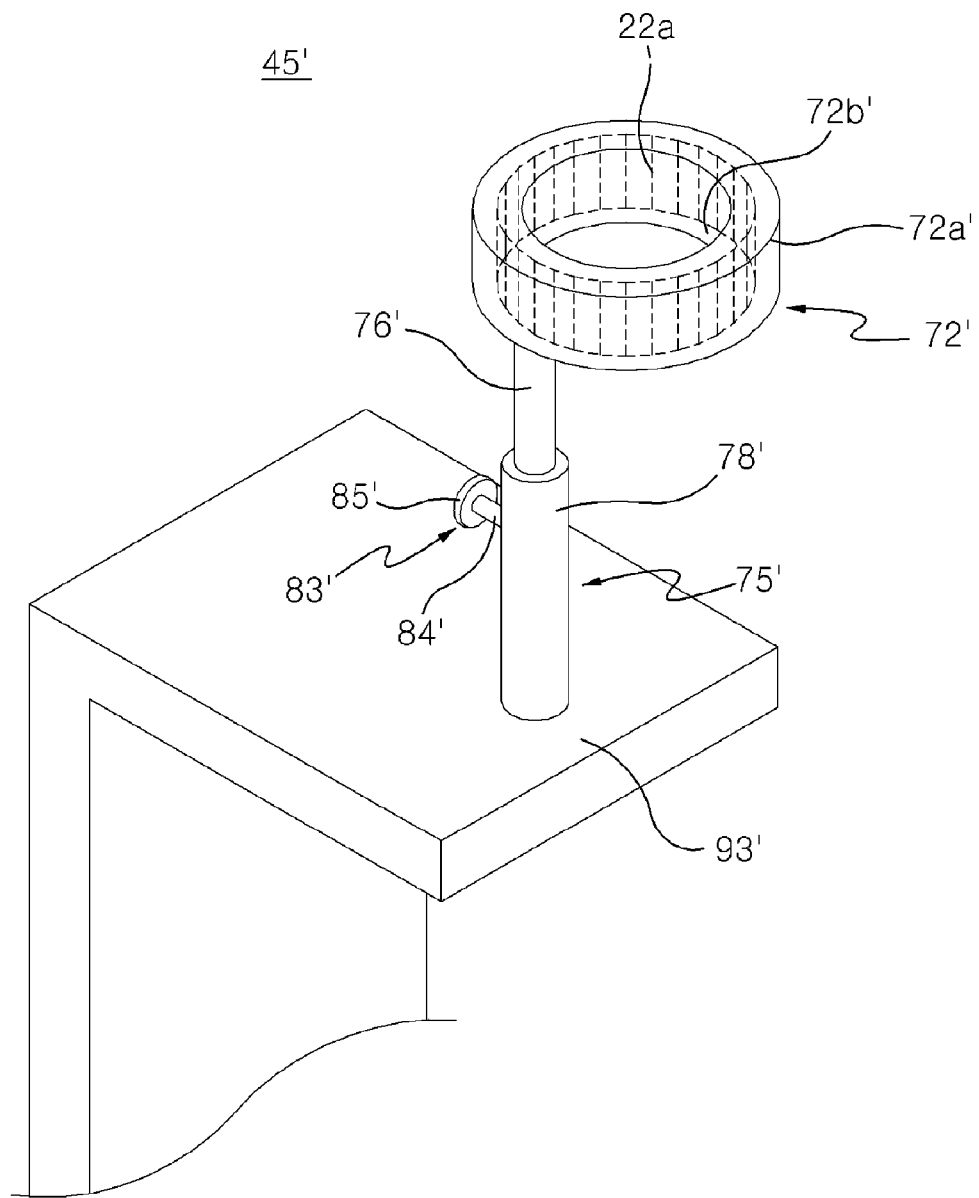
FIG. 17 is a perspective view showing a modification of the vertical movement limiting part of the head-fixing unit of the MRI system of FIG. 1.

As shown in FIG. 17, instead of the hull shape, the main body 72a' may be formed in an annular-shaped or hollow cylinder having a jaw receiving recess 72b'. In this instance, the RF coil 22a is arranged in a cylindrical shape inside the main body 72a'.

Referring to FIG. 16, the support portion 73 includes first and second bars 73a protrudingly formed at the center of upper faces of the right and left side walls of the main body 72a so as to get in contact with the ear portion of the patient 17 to support the patient's head part not to be moved in back and forth and right and left directions. The first and second bars 73a respectively have elasticity and are formed thin below a predetermined diameter so that a round support end portion 73c gets in contact with the ear portion of the patient 17 to support the patient's head part not to be moved in back and forth and right and left directions. The first and second bars 73a are screw-coupled to screw holes 73b formed in the right and left side walls of the main body 72a so as to regulate the height of the round support end portion 73c according to the height of the ear portion of the patient 17.

The jaw rest 72 has an end portion 76a of an arm 76 pivotally fixed at a bottom face of the jaw rest 72 so as to constitute a vertical movement limiting part 45 of the head-fixing unit 44, which limits a vertical movement of the patient's head part.

In this embodiment, the RF coil 22, for instance, may include a two-way RF coil in which an outgoing RF coil and an incoming RF coil are formed integrally. The two-way RF coil includes: a copper plate or a copper bar; a coil which can transmit and receive an Y-axis signal relative to the main magnetic field of a Z-axis direction attached to the copper plate or the copper bar not to be shorted out; another coil which can transmit and receive an X-axis signal; a plurality of capacitors attached to the copper plate or the coils and to the middle of the coils to cause resonance at a wanted frequency; and a combiner 23 connected to each coil through a coaxial line so as to transmit and receive signals outputted from each coil. Because such a configuration of the coils is known in the relevant art field as a bird cage type RF coil, a detailed description thereof will be omitted.

In this embodiment, the RF coil 22 is the bird cage RF coil, but may be a surface attachment type RF coil, which will be described referring to FIGS. 5 to 7 later.

As described above, the RF coil unit 21 includes the support frame assembly 24, which has the jaw rest 72 of the hull shape having the jaw receiving recess 72a, and the RF coils 22 of the bird cage type, which are arranged inside the front and rear and right and left side walls of the jaw rest 72, but may adopt another form.

Figure 5:
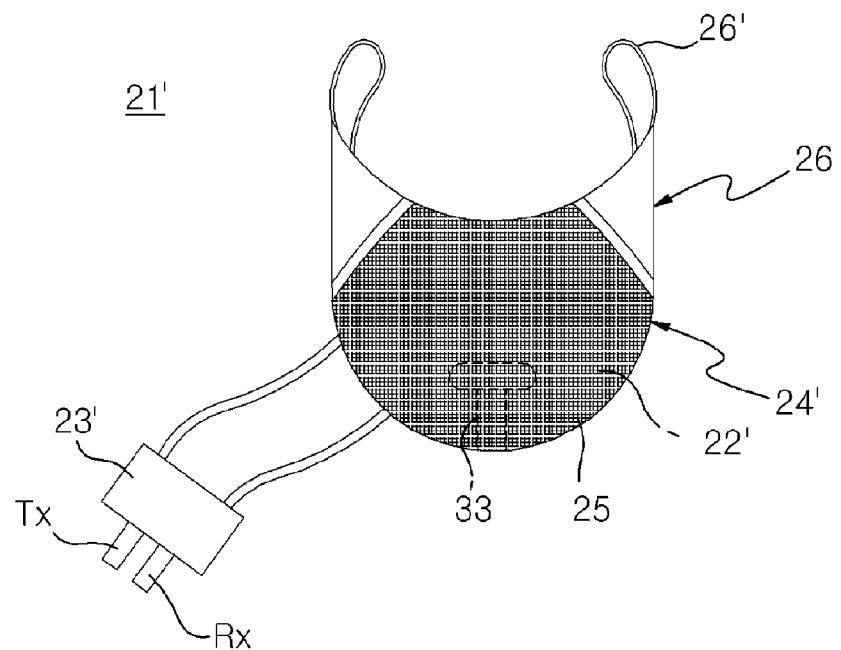
FIGS. 5 to 7 are a perspective view, a plan view and a front view showing a modification of an RF coil unit of the MRI system of FIG. 1.
Figure 6:
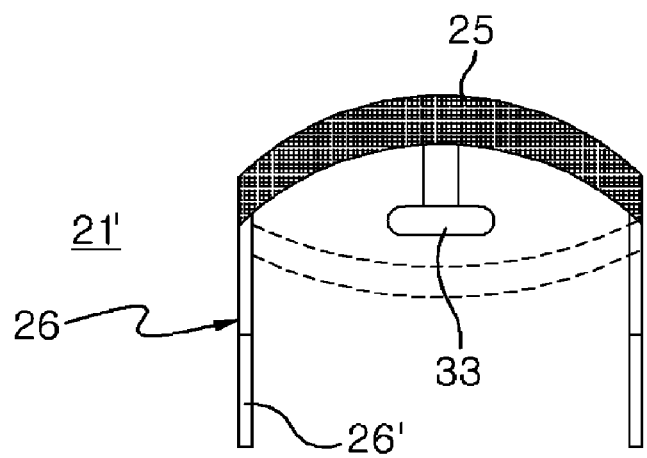
Figure 7:
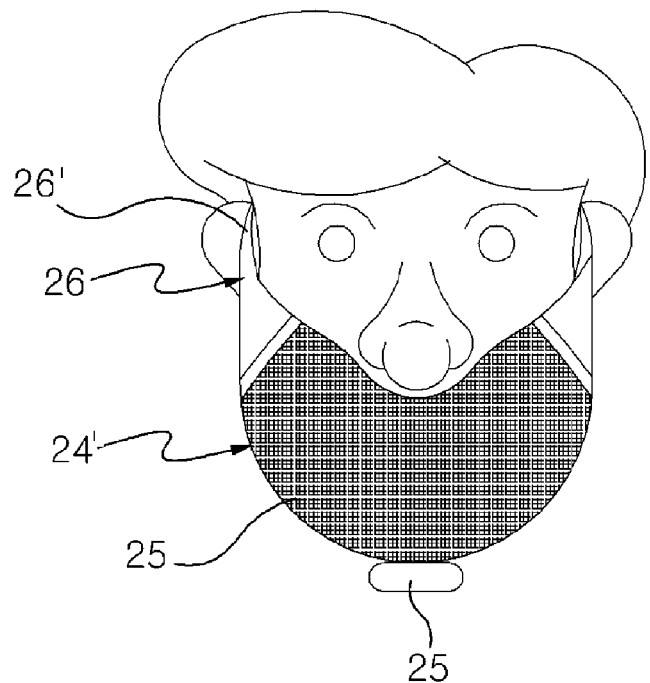

For instance, referring to a modification of FIGS. 5 to 7, the present invention may have an RF coil unit 21' including the surface attachment type RF coil unit. The RF coil unit 21' gets in surface-to-surface contact with an attached part to surround only the front surface of the attached part, and includes a mask 24' in which an RF coil 22' is arranged.

The mask 24' is a support frame assembly in which the RF coil 22' is arranged and supported, and includes a main body 25 corresponding to the attached part and a fixing part 26 formed on the main body 25 for contactingly fixing and maintaining the main body 25 to the attached part.

Like the main body 72a of the jaw rest 72 illustrated in FIG. 16, the main body 25 is made of an insulator having proper mechanical strength to bear an electromagnetic power generated when electric current is applied to the RF coil 22' and to keep the shape corresponding to the attached part. The main body 25 is formed in a round shape, which is in surface-to-surface contact with the attached part and surrounds only the front surface of the attached part. The RF coil 22' is arranged inside the main body 25.

Like the RF coil 22 of the RF coil unit 21, the RF coil 22' includes a two-way RF coil in which an outgoing RF coil and an incoming RF coil are formed integrally. The two-way RF coil, for instance, includes: a copper plate having a predetermined width; a one-loop type coil which can transmit and receive an Y-axis signal relative to the main magnetic field of a Z-axis direction attached to the copper plate not to be shorted out; a butterfly loop type coil which can transmit and receive an X-axis signal; a plurality of capacitors attached to the middle of the copper plate and/or the coils to cause resonance at a wanted frequency; and a combiner 23 connected to each coil through a coaxial line so as to transmit and receive signals outputted from each coil. Because such a configuration of the coils is known in the relevant art field as the surface attachment type RF coil, a detailed description thereof will be omitted.

The fixing part 26 includes an ear holding portion 26' formed on the main body 25 so that the main body 25 can be help to the patient's ear part.

In order to stably keep a state where the main body 25 is in close contact with the attached part when the fixing part 26 fixes the main body 25 to the patient's ear part, the main body 25 for supporting the patient's jaw part has a jaw support 33 protrudingly formed on a bottom face of the main body 25.

Like the main body 73a of the jaw rest 72 illustrated in FIG. 16, the jaw support 33 of the mask 24' has an end portion 76a of an arm 76 pivotally fixed at a bottom face of the jaw support 33 so as to constitute a vertical movement limiting part 45 of the head-fixing unit 44, which limits a vertical movement of the patient's head part.

Because the RF coil unit 21 having the above structure is formed in a round shape so that the main body 25 is in direct surface-to-surface contact with the attached part, the RF coil unit 21 can obtain a signal-to-noise ratio higher than the RF coil unit 21 illustrated in FIG. 16, which is not completely in surface-to-surface contact with the attached part, and hence, can obtain more accurate and clear MR images.

Figure 8:
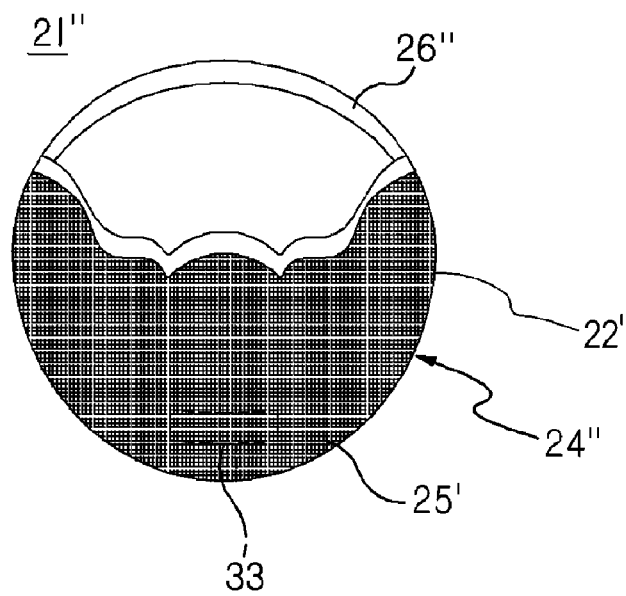
FIGS. 8 to 10 are a perspective view, a plan view and a front view showing another modification of an RF coil unit of the MRI system of FIG. 1.
Figure 9:
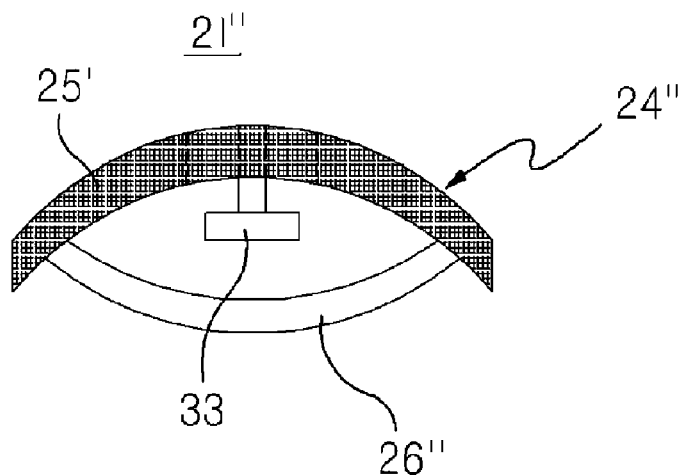
Figure 10:
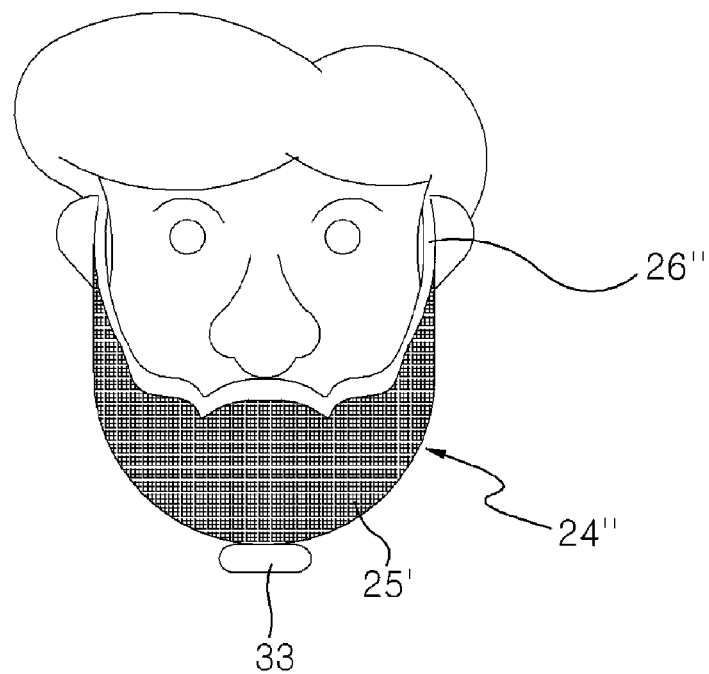

Referring to FIGS. 8 to 10, like the RF coil unit 21' illustrated in FIGS. 5 to 7, another RF coil unit 21" according to another modification of the surface attachment type RF coil unit is illustrated. The RF coil unit 21" is equal to the RF coil unit 21' illustrated in FIGS. 5 to 7, excepting that a portion, where the RF coil 22' is arranged, of a main body 25' of a mask 24" is expanded to the vicinity of the ear part and the fixing part 26" is an elastic band connected to the main body 25' so as to elastically fix the main body 25' to the head part.

Figure 11:
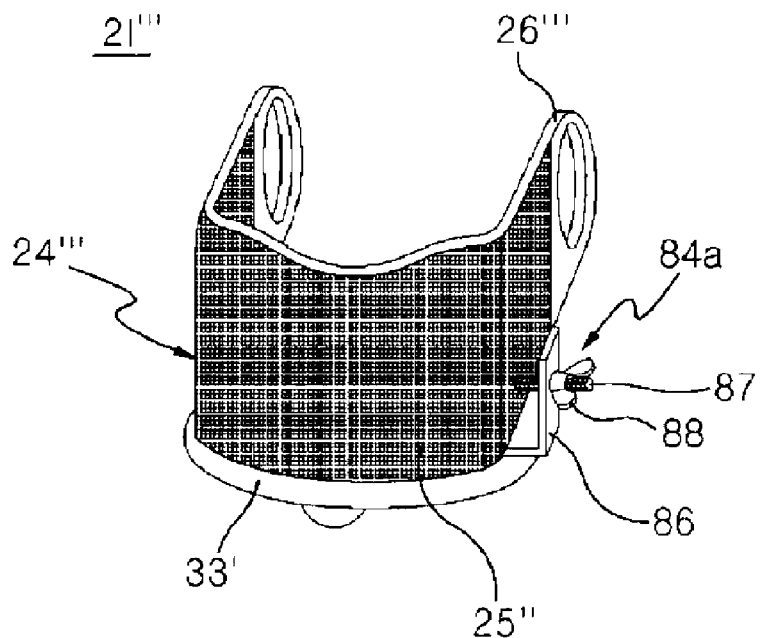
FIGS. 11 to 13 are a perspective view, a plan view and a front view showing a further modification of an RF coil unit of the MRI system of FIG. 1.
Figure 12:
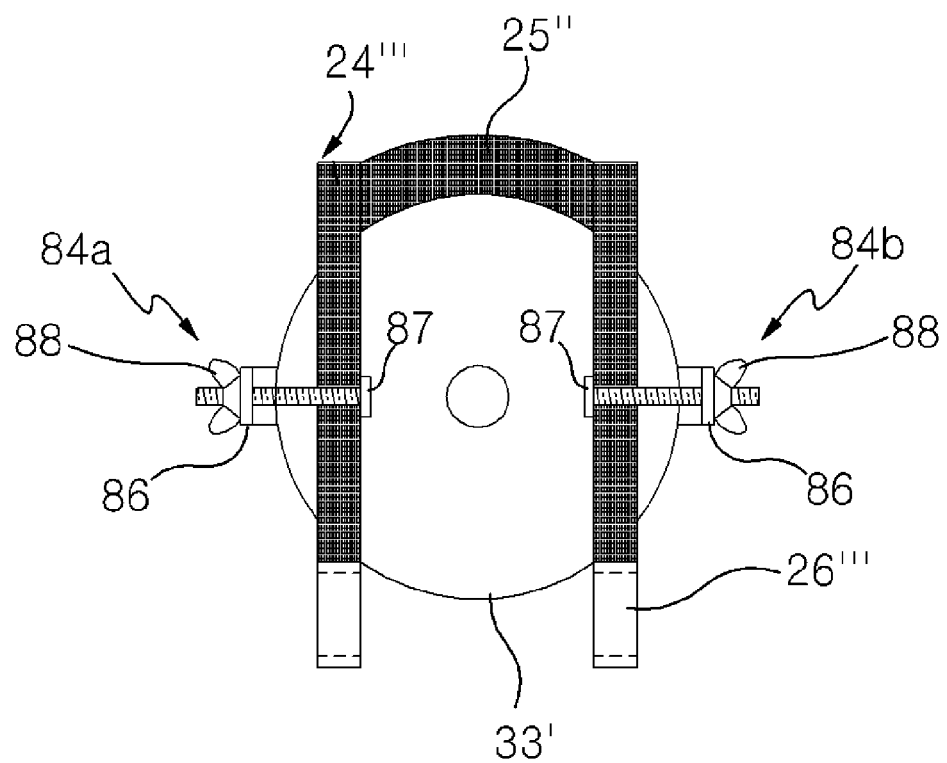
Figure 13:
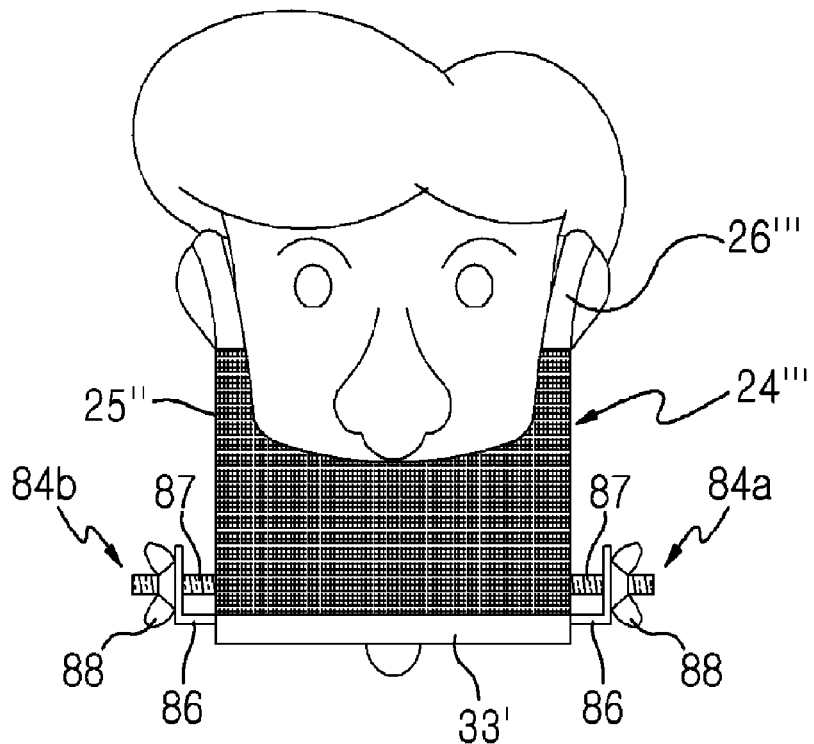

Referring to FIGS. 11 to 13, like the RF coil unit 21' illustrated in FIGS. 5 to 7, an RF coil unit 21'" having the surface attachment type RF coil unit according to a further modification is illustrated. In the RF coil unit 21'", a mask 24'" includes a main body 25" formed not in the round shape but in a "⌐" shape or a "U" shape to surround the front face and sides including ears of the attached part. The main body 25" includes fixing parts 26'" constructed of ring-shaped elastic bands and formed at read end portions of both sides thereof. A jaw support 33' is formed on the bottom face of both side portions of the main body 25". An end portion 76a of an arm 76 may be pivotally fixed to the bottom face of the jaw support 33', like the jaw support 33 of the mask 24' and the main body 73a of the jaw rest 72.

First and second distance-adjusting parts 84a and 84b are formed between both side portions of the main body 25" and the jaw support 33' to connect the both side portions of the main body 25" and the jaw support 33' with each other and regulate a distance between the both side portions of the main body 25" according to the size of the jaw part of the patient 17. Each of the first and second distance-adjusting parts 84a and 84b includes: an L-shaped bracket 86 protrudingly formed on a side of the jaw support 33'; a screw portion 87 having an end portion supporting the inner face of the side portion of the main body 25" and the other end portion passing through holes formed in the bracket 86 and the side portion of the main body 25" and protruding to the outside; and an adjustable nut 88 screw-coupled with the other end portion of the screw portion 87. Therefore, if the size of the jaw part of the patient 17 is longer than the previously adjusted distance between both side portions of the main body 25", when the adjustable nuts 88 of the first and second distance-adjusting parts 84a and 84b are tightened, the side portions of the main body 25" move toward the outside corresponding to the tightened adjustable nuts 88, such that the distance between both side portions of the main body 25" is widened. On the contrary, if the size of the jaw part of the patient 17 is shorter than the previously adjusted distance between both side portions of the main body 25", when the adjustable nuts 88 of the first and second distance-adjusting parts 84a and 84b are loosened, the side portions of the main body 25" move toward the inside corresponding to the loosened adjustable nuts 88 by self-elasticity, such that the distance between both side portions of the main body 25" is narrowed.

As described above, the main body 72a of the jaw rest 71 and the main bodies 25, 25' and 25" of the masks 24', 24" and 24'" are formed corresponding to the attached part including the jaw part excepting the patient's nose part, namely, the patient's face part on which the teeth and the gums are located, but the present invention is not restricted to the above. For instance, for more accurate diagnosis and otolaryngological diagnosis of the teeth and the gums, the main bodies 72a, 25, 25' and 25" may be formed corresponding to the attached part including the nose part and the jaw part.

Figure 14:
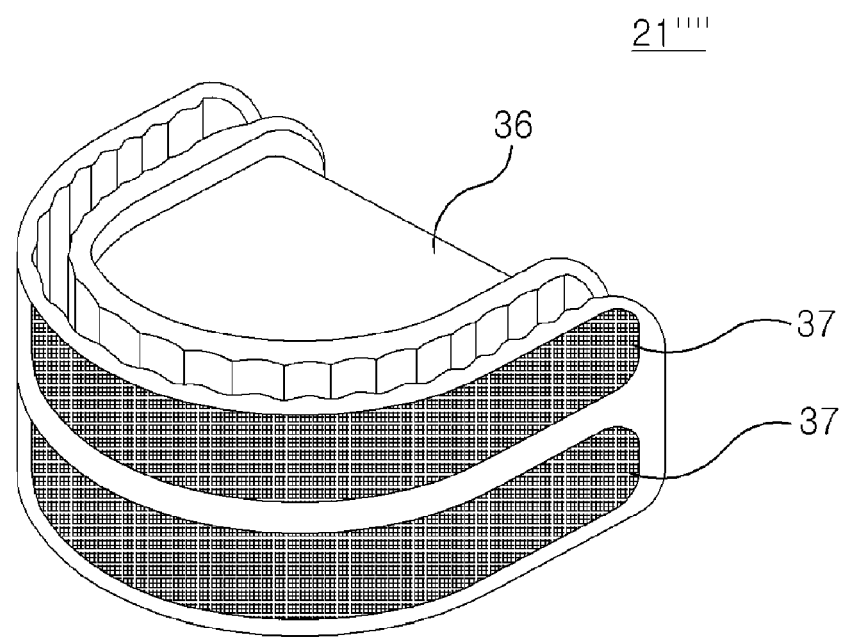
FIG. 14 is a perspective view showing a still further modification of an RF coil unit of the MRI system of FIG. 1.

Moreover, the main bodies 72, 25, 25' and 25" are attached to the attached part, namely, the patient's face part where the teeth and the gums are located, but the present invention is not restricted to the above. For instance, as shown in FIG. 14, an RF coil unit 21"" may be directly attached to the teeth and the gums. For this, the support frame assembly 36 may include an RF coil 37, which has a two-way RF coil and is arranged inside the outer face of the support frame assembly, and a mouth piece having a form corresponding to the teeth and the gums. Here, the mouth piece has the form that surrounds all of the inside and the outside of the teeth, but may have a C-shaped plate form that surrounds only the outside of the teeth.

Furthermore, the RF coil units 21, 21', 21", 21'" and 21"" respectively have the two-way RF coils 22, but may include an outgoing RF coil and an incoming RF coil which are formed separately. In this instance, the RF coil unit may be constructed in such a fashion that the outgoing RF coil is disposed at the main body 72a of the jaw rest 72 illustrated in FIG. 16 and the incoming RF coil is arranged in the main body 25, 25' or 25" of the mask 24', 24" or 24'" illustrated in FIG. 5 to 13 or in the mouth piece illustrated in FIG. 14. Alternatively, the RF coil unit may be constructed in such a fashion that the outgoing RF coil is disposed at the main body 25, 25' or 25" of the mask 24', 24" or 24'" illustrated in FIGS. 5 to 13 and the incoming RF coil is arranged in the mouth piece illustrated in FIG. 14. Of course, the RF coil unit may be comprised of the outgoing RF coil arranged at a separate support frame assembly (not shown), which surrounds the patient's head part, and the incoming RF coil arranged at the main body 72a of the jaw rest 72 illustrated in FIG. 16, the main bodies 25 and 25' or 25" of the mask 24' and 24" or 14'" illustrated in FIGS. 5 to 13, or the mouth piece illustrated in FIG. 14. The structures of the outgoing RF coil and the incoming RF coil are known in the relevant art field, and hence, detailed descriptions of the structures will be omitted.

Referring to FIG. 1, the RF coil driving unit 40 operates the RF coil 21 under the control of the data processing unit 70 so as to apply an RF pulse to the examined part of the patient, namely, the teeth and the gums, and hence, forms a high-frequency magnetic field for causing a spin on particles inside the examined part. At the same time, the RF coil driving unit 40 operates the RF coil 21 to detect an MR signal, which is an electromagnetic wave generated by the spin of the particles inside the examined part of the patient.

In order to prevent detection of a bad MR signal due to the patient's movement, as shown in FIGS. 3, 4, 15 and 16, the MRI system 1 according to the present invention may further include a head-fixing unit 44 for fixing the patient's head part not to be moved during the examination.

The head-fixing unit 44 is arranged on a stand 93 (see FIGS. 3a and 3b) mounted at an upper portion of the backrest 14a of the chair 14 of the examination table 10 and at one side of the chair 14. The head-fixing unit 44 includes a lateral movement limiting part 48 for limiting backward and lateral movements of the head, and a vertical movement limiting part 45 for limiting a vertical movement of the head.

Figure 15:
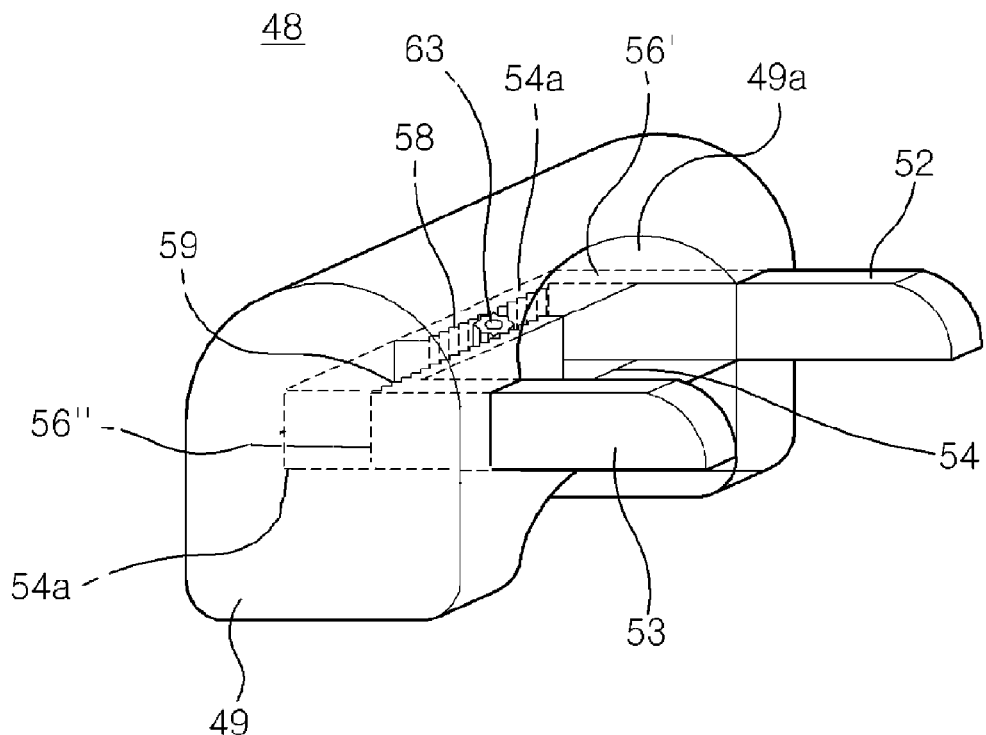
FIG. 15 is a perspective view of a lateral movement limiting part of a head-fixing unit of the MRI system of FIG. 1.

As shown in FIG. 15, the lateral movement limiting part 48 includes a head rest 49, first and second head bars 52 and 53, and a guide rail 54.

The head rest 49 is fixed at the upper portion of the back rest 14a of the chair 14 and has a semicircular concave hole 49a formed in a front face thereof for receiving the rear part of the head. Here, it is described that the head rest 49 is fixed at the upper portion of the backrest 14a of the chair 14, but may be vertically moved at the upper portion of the backrest 14a using a known fixing means (not shown).

The first and second head bars 52 and 53 for supporting the left side part and the right side part of the head respectively include guides 56' and 56" respectively formed at rear end portions thereof in such a way as to be accommodated and supported in the guide rail 54 in a movable manner. The guide rail 54 includes a rail groove 54a formed in the head rest 49 to support the guides 56' and 56" of the first and second head bars 52 and 53 in a movable manner.

Figure 18:
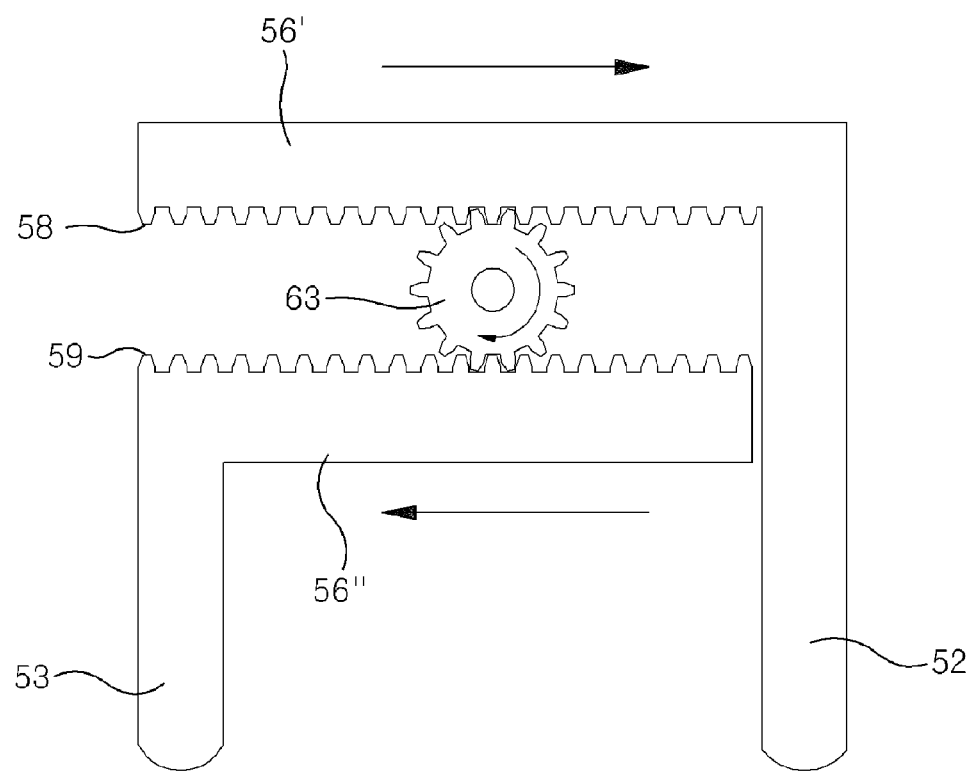
FIG. 18 is a plan view showing a rack and a pinion of the lateral movement limiting part of FIG. 15.

As shown in FIG. 18, in order to make the first and second head bars 52 and 53 get closer to each other or get farther apart from each other by moving the first head bar 52 in one direction and the second head bar 53 in the other direction, the lateral movement limiting part 48 may further include first and second racks 58 and 59 respectively formed on the guides 56' and 56" of the first and second head bars 52 and 53, and a pinion 63 arranged between the first and second racks 58 and 59 inside the rail groove 54a.

Figure 3:
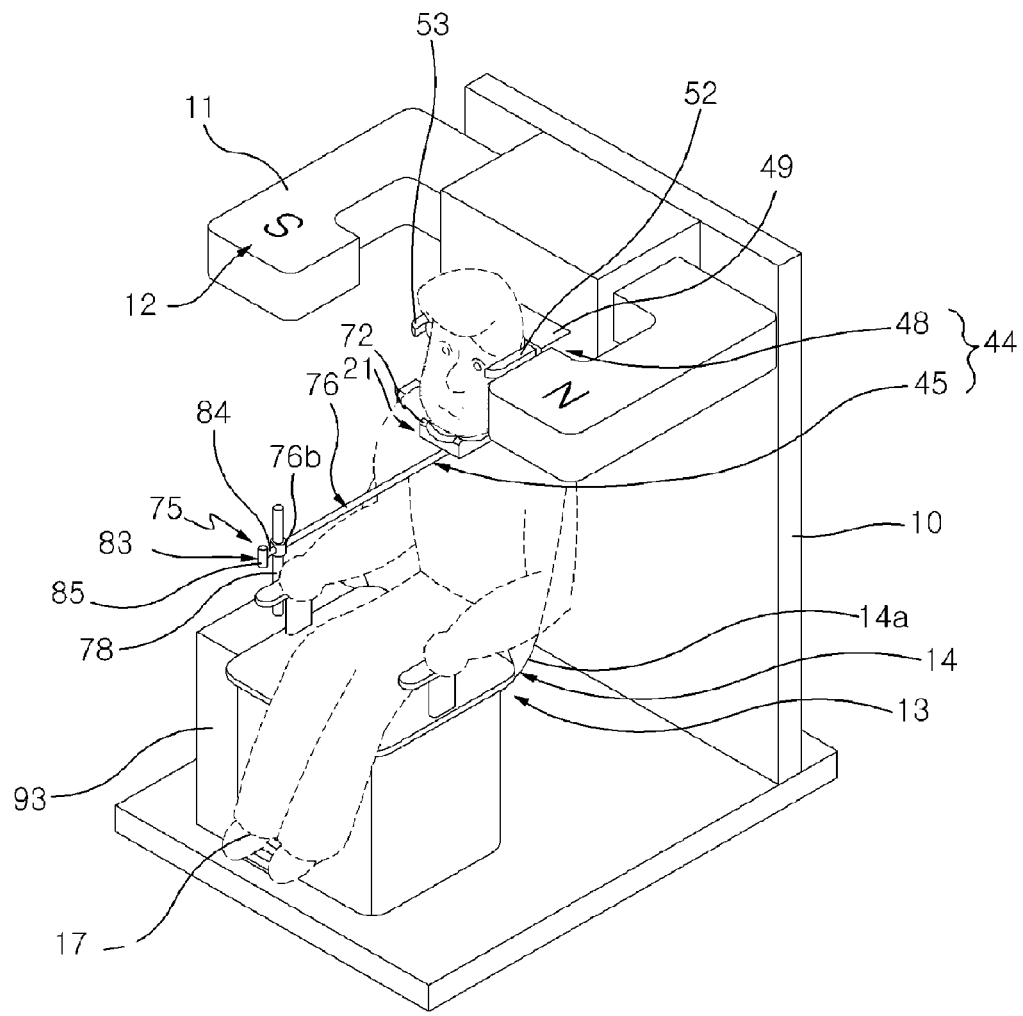
FIGS. 3 and 4 are perspective views showing actions of the MRI system of FIG. 1.
Figure 4:
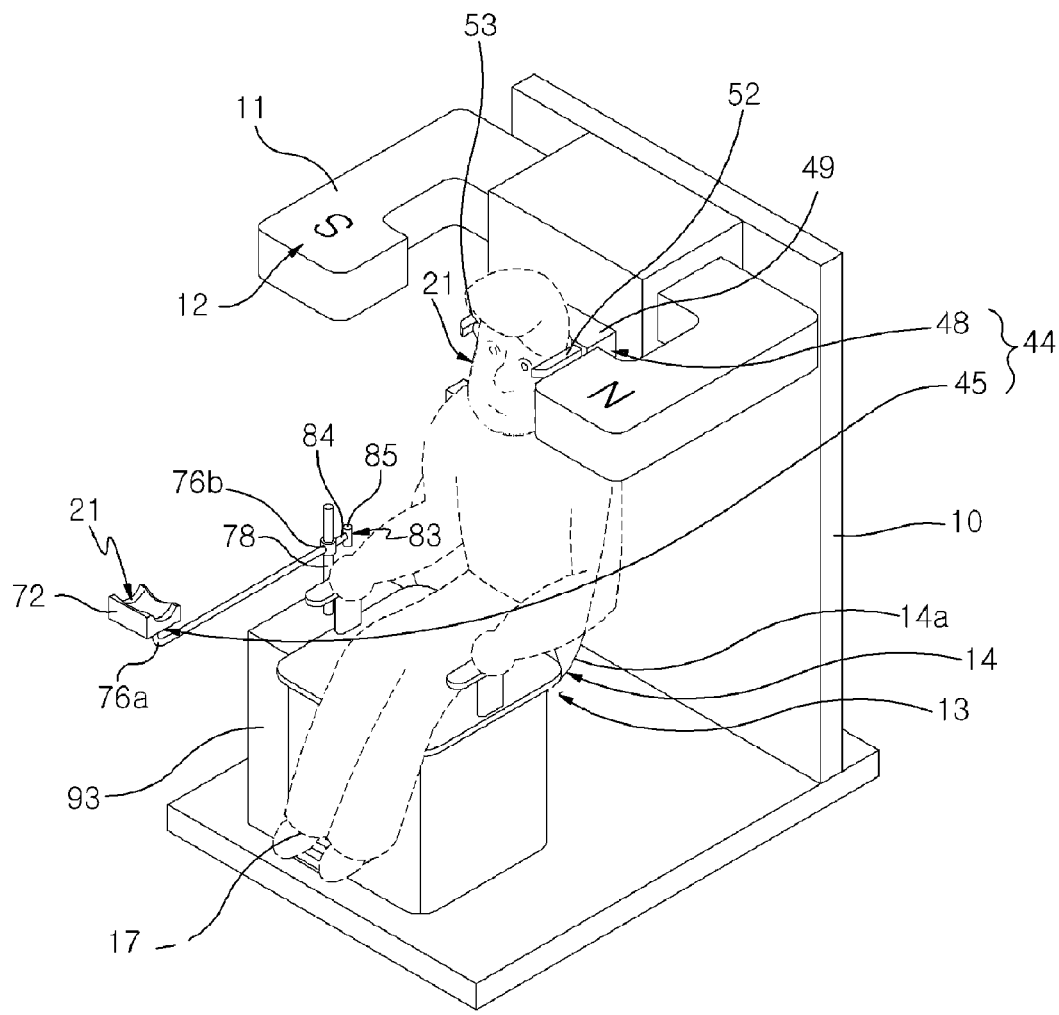

As shown in FIGS. 3 and 4 and 16, the vertical movement limiting part 45 includes the jaw rest 72 and a jaw rest moving part 75. As described above, the jaw rest 72 includes the jaw receiving recess 72a (see FIG. 16) for supporting the patient's jaw part. The jaw rest moving part 75 fixes the jaw rest 72 and moves the jaw rest 72 between a storing position (FIG. 3b) and a jaw supporting position (FIG. 3a), and includes an arm 76 having an end portion 76a for pivotally fixing the jaw rest 72. The arm 76 is formed in a hollow bar shape. The other end portion 76b of the arm 76 is supported on a pivot shaft 78 formed on the stand 93 positioned besides the chair 14 to move the arm 76 between the storing position and the jaw supporting position. A clamp 83 includes a screw portion 84 and a knob 85 fixed in a screw hole (not shown) of a boss formed at the other end portion 76b of the arm 76. The clamp 83 moves the arm 76 vertically, and then, tightens the screw portion 84 to the screw hole using the knob 85, so that a front end of the screw portion 84 gets in compressed contact with the pivot shaft 78 to fix the arm 76 at the moved position.

Selectively, as shown in FIG. 17, a vertical movement limiting part 45' may include a jaw rest 72' and a jaw rest moving part 75'. As described above, the jaw rest 72' includes an annular or cylindrical main body 72a', in which the RF coil 22a is arranged, and which has a jaw receiving recess 72b'. The jaw rest moving part 75' includes a support bar 76' fixed at a lower portion of the main body 72a' to support the main body 72a', and a receiving bar 78' for receiving the support bar 76' and supporting the support bar 76' in such a way as to move vertically and rotate. A lower part of the receiving bar 78' is fixed to the stand 93' located beside the chair 14 and a clamp 83' for fixing the support bar 76' not to be moved is formed at an upper part of the receiving bar 78'. The clamp 83' includes a screw portion 84' and a knob 85' fixed to a screw hole (not shown) formed in the upper portion of the receiving bar 78', and tightens the screw portion 84' to the screw hole using the knob 85', so that a front end of the screw portion 84' gets in compressed contact with the support bar 76' to fix support bar 76' at the moved position.

Referring to FIG. 1, the data collecting unit 30 collects an MR signal detected from the RF coil unit 21 under the control of the control unit 60 and outputs the signal to the data processing unit 70. The data processing unit 70 has a computer having a memory in which an MRI processing program is stored. The data processing unit 70 creates an image from the received MR signal in cooperation with the control unit 60 according to the MRI processing program stored in the memory, computes a differential of the created image signal, and processes necessary data relative to the differential image. The data processing unit 70 displays the processed result on the display unit 80, such as a monitor, as an MR image of the examined part.

The control unit 60 controls the gradient coil driving unit 50, the RF coil driving unit 40, and the data collecting unit 30 according to a control value inputted in a memory of the control unit 60 through the data processing unit 70 by a user's input through the operation unit 90, such as a keyboard, in cooperation with the data processing unit 70, and hence, controls imaging of the examined part, which is the teeth and the gums, of the patient 17.

Referring to FIGS. 1, 3 and 4, the actions of the MRI system 1 will be described as follows.

First, after the patient 17 sits on the chair 14 located on the cradle 13 of the examination table 10, the chair 14 is adjusted in such a fashion that the patient's head part is positioned between the imaging spaces 16 by the angle-adjusting means of the backrest 14a and/or the back and forth moving means of the cradle 13.

Continuously, the patient 17 corrects the posture in such a fashion that the head part leans against the semicircular concave hole 49a of the head rest 49 fixed at the upper portion of the backrest 14a of the chair 14, and then, when the first and second head bars 52 and 53 are moved laterally, so that the left and right parts of the head part are fixed not to be moved laterally.

After that, in order to make the RF coil unit 21 mounted on the jaw rest 72 get in close contact with the patient's attached part, namely, the patient's face part where the teeth and the gums are positioned and to prevent the patient's head part from moving vertically, the user loosens the other end portion 76b of the arm 76 fastened to the pivot shaft 78 by manipulating the clamp 83, and then, moves the arm 76, which fixes the jaw rest 72, pivotally rotates on the pivot shaft 78 to thereby move from the storing position (FIG. 4) to the jaw supporting position (FIG. 3a). Next, the jaw rest 72 is vertically moved together with the arm 76 along the pivot shaft 78 and pivoted relative to one end portion 76a of the arm 76, such that the patient's jaw part is supported by the jaw receiving recess 72a of the jaw rest 72. After that, the other end portion 76b of the arm 76 is fixed by manipulation of the clamp 83.

Next, in order to operate the MRI system 1, the user inputs an operation order to the data processing unit 70 through the operation unit 90.

According to the operation order, the data processing unit controls the gradient coil driving unit 50 according to a preset control value in cooperation with the control unit 60. As a result, the gradient coil 15 forms a magnetic field having a magnetic variation slope of X, Y and Z directions inside the main magnetic field generated by the magnetic assembly 12. Moreover, the data processing unit 70 and the control unit 60 actuate the shim coil unit 18 through the shim coil driving unit 50 to make the main magnetic field uniform. Additionally, the data processing unit 70 and the control unit 60 actuate the RF coil 21 through the RF coil driving unit 40 to apply the RF pulse to the examined part to form the high-frequency magnetic field inside the teeth and the gums, which are the examined part of the patient 17, and at the same time, actuate the RF coil 21 to continuously detect the MR signal from the patient's examined part.

Furthermore, the data processing unit 70 and the control unit 60 actuate the lifting unit 27 in order to move the patient's examined part into the imaging space 16. Accordingly, the patient's examined part is gradually moved into the imaging space 16 of the magnetic assembly 12 as the chair 14 is lifted, for instance, upwardly by the lifting unit 27.

The data collecting unit 30 continuously outputs the MR signal, which is continuously outputted from the RF coil 21, to the data processing unit 70. The data processing unit 70 stores the inputted MR signal to the memory and operates the MRI processing program. After that, the data processing unit 70 displays the MR imagines on the display unit 80.

While the present invention has been described with reference to the particular illustrative embodiments, it should be understood, however, that there is no intent to limit the example embodiment of the present invention to the particular forms disclosed. It will be understood that the example embodiments of the present invention is to cover all modifications, equivalents, and alternatives without departing from the spirit and scope of the invention as defined by the appended claims.

The invention claimed is:

1. An RF (Radio Frequency) coil unit comprising:
   an RF coil; and
   a support frame assembly in which the RF coil is supported, the support frame assembly being formed corresponding to an attached part including at least one of a patient's teeth and gums and the patient's face part where the teeth and gums are positioned, wherein the support frame assembly comprises: one of a jaw rest having a jaw receiving recess formed corresponding to the face part, in which the patient's teeth and gums are positioned, and which includes the patient's jaw; a mask formed corresponding to the face part, in which the patient's teeth and gums are positioned; and a mouth piece formed corresponding to the patient's teeth and gums.

2. The RF coil unit according to claim 1, wherein the jaw rest comprises:
   a main body having a jaw receiving recess; and a support portion for supporting the patient's head not to be moved.

3. The RF coil unit according to claim 1, wherein the mask comprises:
   a main body formed corresponding to the face part, in which the patient's teeth and gums are positioned; and
   a fixing part formed on the main body for fixing the main body corresponding to the face part, in which the patient's teeth and gums are positioned.

* * * * *